United States Patent [19]

Koga et al.

[11] 4,242,272

[45] Dec. 30, 1980

[54] SUBSTITUTED PHENETHYLDICHLOROSILANES AND METHOD FOR PRODUCING SAME

[75] Inventors: Isao Koga, Yokohamashi; Yohji Terui, Chibashi; Masuhito Ohgushi; Tohru Kitahara, both of Minamatashi, all of Japan

[73] Assignee: Chisso Corporation, Osaka, Japan

[21] Appl. No.: 915,654

[22] Filed: Jun. 15, 1978

[51] Int. Cl.$^3$ .............................................. C07F 7/08
[52] U.S. Cl. .................................................. 556/489
[58] Field of Search ................. 260/448.2 E, 448.2 R

[56] References Cited

U.S. PATENT DOCUMENTS

| | | | |
|---|---|---|---|
| 3,856,837 | 12/1974 | Chandra | 260/448.2 E X |
| 3,992,427 | 11/1976 | Chandra et al. | 260/448.2 E |

*Primary Examiner*—Paul F. Shaver
*Attorney, Agent, or Firm*—Fred Philpitt

[57] ABSTRACT

Substituted phenethyldichlorosilanes having a longer chain alkyl group and diphenethyldichlorosilane which are useful as compounds for improving heat-resisting property and other properties of silicone-oils, -rubbers and -varnishes which are used as electric insulating materials, lubricating oils, water-repelling agents, paintings, releasing agents, etc. are provided. A method for producing these compounds with a high yield without producing by-products is also provided.

3 Claims, 6 Drawing Figures

SUBSTITUTED PHENETHYLDICHLOROSILANES AND METHOD FOR PRODUCING SAME

DESCRIPTION OF THE INVENTION

This invention relates to diorganodichlorosilanes. More particularly, it relates to substituted phenethyldichlorosilanes and a method for producing same. Diorganodichlorosilanes are very important compounds in silicone resin industry but compounds which are used actually in industry are relatively few, such as dimethyldichlorosilane, diphenyldichlorosilane, etc. As for methods for producing these compounds, there have been known a method which utilizes Rochow's process and a method which utilizes Grignard reaction, but any of these methods produce a large amount of by-product and it is difficult to obtain diorganodichlorosilanes with good yield according to these methods.

On the other hand, with the recent development of silicone resin industry, compounds which have not been known have become necessary. However, it would be difficult to obtain objective compounds according to conventional methods such as Rochow's process or the like.

For example, compounds (which will be referred to as $R^1R^2SiCl_2$) which contain an alkyl group ($R^1$) on one hand and an aralkyl group ($R^2$) on the other hand are useful as bifunctional monomers for polysiloxanes. However, $R^1R^2SiCl_2$ which has been produced heretofore commercially is only $CH_3SiCl_2Ph$ (wherein Ph is a phenyl group), and as others, only compounds in which $R^1$ is methyl group or ethyl group, and which are indicated by $C_2H_5SiCl_2(CH_2CH_2Ph)$, $C_2H_5SiCl_2(CHCH_3Ph)$, $C_2H_5SiCl_2[(CH_2)_3Ph]$, $C_2H_5SiCl_2[CH_2CH(CH_3)Ph]$, $C_2H_5SiCl_2[(CH_2)_4Ph]$, and $C_2H_5SiCl_2[CH(CH_3)CH_2CH_2Ph]$, are found in Chemical Abstracts vol. 54 page 22435, and vol. 53 page 17028. It is the present status of art that there are no compound of $R^1R^2SiCl_2$ having a long chain alkyl group $R^1$ nor diphenethyldichlorosilane, and neither production method of these compounds.

We have been repeating research works in various ways in order to overcome the above-mentioned problem in this field of art and succeeded in the preparation of compounds which have never been known.

Thus an object of the present invention is to provide a method for producing substituted phenethyldichlorosilanes. More particuarly, it is a first object to provide alkylphenethyldichlorosilanes having a longer chain alkyl group, it is a second object to provide diphenethyldichlorosilanes, it is a third object to provide a method for producing these compounds and it is a fourth object to provide novel silicone resins by utilizing these compounds.

The compounds of the present invention are substituted phenethyldichlorosilanes represented by the general formula

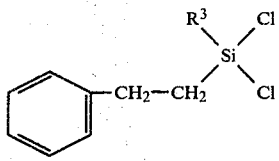

(1)

wherein $R^3$ is an alkyl group having 3–20 carbon atoms or phenethyl group. More particularly, they include firstly alkylphenethyldichlorosilanes represented by the general formula

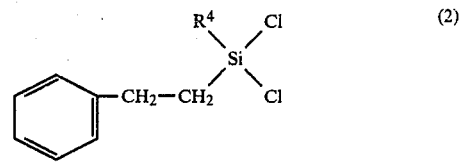

(2)

wherein $R^4$ is an alkyl group having 3–20 carbon atoms.

As concrete names of the compounds of the above-mentioned formula (2), propylphenethyldichlorosilane, isopropylphenethyldichlorosilane, butylphenethyldichlorosilane, isobutylphenethyldichlorosilane, pentylphenethyldichlorosilane, isoamylphenethyldichlorosilane, hexylphenethyldichlorosilane, heptylphenethyldichlorosilane, octylphenethyldichlorosilane, nonylphenethyldichlorosilane, decylphenethyldichlorosilane, undecylphenethyldichlorosilane, dodecylphenethyldichlorosilane, tridecylphenethyldichlorosilane, tetradecylphenethyldichlorosilane, hexadecylphenethyldichlorosilane, octadecylphenethyldichlorosilane, eicosylphenethyldichlorosilane, can be mentioned.

The compounds of the invention also include secondarily diphenethyldichlorosilane represented by the formula

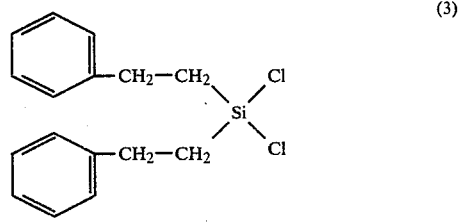

(3)

A first method for producing the compounds of the present invention is characterized in reacting a monosubstituted dichlorosilane represented by the general formula $R^3HSiCl_2$ (wherein $R^3$ is an alkyl group having 3~20 carbon atoms or phenethyl group) with styrene in the presence of a complex of platinum and a phosphine compound at a temperature of 30°~200° C.

A second method for producing the compounds of the present invention is characterized in reacting dichlorosilane and an α-olefin compound having 3~20 carbon atoms or styrene to effect addition reaction, in the presence of a complex of platinum and a phosphine compound at 30°~200° C. to form a monosubstituted dichlorosilane having the general formula $R^3HSiCl_2$ wherein $R^3$ is an alkyl group of 3~20 carbon atoms or phenethyl group and then reacting further said reacted liquid with styrene.

More particularly, the method of producing an alkylphenethyldichlorosilane (2) of the present invention comprises reacting a monoalkyldichlorosilane represented by the general formula $R^4HSiCl_2$ (wherein $R^4$ is alkyl having 3 to 20 carbon atoms) and styrene in the presence of a complex of platinum-phosphine compound at a temperature of 30° to 200° C., preferably 30° to 110° C. A reaction time of 1 to 60 hours may be arbitrarily employed. The monoalkyldichlorosilane $R^4HSiCl_2$ is preferably a product of the addition reaction of dichlorosilane with an α-olefin having 3 to 20 carbon atoms. For example, it can be obtained by reacting dichlorosilane and an α-olefin having 3 to 20 carbon atoms in the presence of a complex of a phosphine compound and a transition metal of the VIII group at a temperature of 50° to 200° C. for 1 to 60 hours under atmospheric pressure or under a pressurized condition. Other methods of producing alkylphenethyldichlorosilanes of the present invention include the addition reaction of dichlorosilane with an α-olefin compound having 3 to 20 carbon atoms in the presence of a complex of platinum-phosphine compound at 30° to 110° C., followed by addition of styrene to the reacted liquid to conduct further reaction.

The diphenethyldichlorosilane (3) of the present invention is produced by reacting dichlorosilane or/and monophenethyldichlorosilane with styrene in the presence of a complex of platinum-phosphine compound at 30° to 200° C. This reaction is represented by the following equation (4) or (5):

$$H_2SiCl_2 + 2PhCH=CH_2 \rightarrow (PhCH_2CH_2)_2SiCl_2 \quad (4)$$

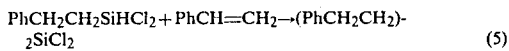

$$PhCH_2CH_2SiHCl_2 + PhCH=CH_2 \rightarrow (PhCH_2CH_2)_2SiCl_2 \quad (5)$$

Namely, the amount of styrene is twice or more in molar ratio to dichlorosilane and equimolar or more to phenethyldichlorosilane. The reaction time, although not specifically defined, ranges preferably within 0.5 to 60 hours.

Monophenethyldichlorosilane used is obtained by reacting dichlorosilane and an equimolar or an excessive amount of styrene in the presence of a complex of a VIII group transition metal and a phosphine compound, for example, chlorotris(triphenylphosphine)rhodium (I) [RhCl(PPh$_3$)$_3$]. When reaction is conducted in the presence of tetrakis(triphenylphosphine)platinum (O) [Pt(PPh$_3$)$_4$], monophenethyldichlorosilane alone is obtained if the molar ratio of styrene to dichlorosilane is one or smaller than one, while diphenethyldichlorosilane is also produced if styrene is excessive.

The complex of platinum and a phosphine compound used in the present invention is preferably tetrakis(triphenylphosphine)platinum (O) [Pt(PPh$_3$)$_4$], and its used concentration is 1 to $10^{-15}$, preferably 1 to $10^{-8}$ mol percent to silicon atom.

The characteristic feature of the production method of the present invention is the use of dichlorosilane or/and mono-substituted dichlorosilane as a starting material for substituted phenethyldichlorosilane production. Further the hydrogen combined with silicon of dichlorosilane or mono-substituted dichlorosilane is added only to the α-position of styrene to form a substituted phenethyldichlorosilane.

Namely, the fact that an isomer in which the above-defined hydrogen is added to the β-position of styrene and by-products of styrene polymer are not formed as by-products, is a great advantage, and the objective substituted phenethyldichlorosilane is formed with an extremely high yield.

The production method of the present invention can be carried out in either of the type of the apparatuses of batch system, flow method system, and half batch system. For example, in case of production of diphenethyldichlorosilane a method in which liquefied dichlorosilane, styrene and a catalyst are charged into a sealed reactor and reacted by heating under a pressure and a product is obtained by distillation after the reaction, a method in which dichlorosilane is flown into a reaction vessel containing styrene and a catalyst liquid and a method in which styrene and dichlorosilane are counter-flown through a fixed bed supporting a catalyst on a carrier can be used.

The compounds of the present invention are novel compounds and useful as compounds for improving heat-resisting property and other properties of silicone oils, rubbers and varnishes which are used as electric insulating materials, lubricating oils, water-repelling agents, paintings, releasing agents, etc.

The present invention will be illustrated by way of specific examples, but they are not intended to limit the scope of the invention.

EXAMPLE 1

3.80 g (20.5 millimol) of n-hexyldichlorosilane, 2.00 g (19.2 millimol) of styrene, and 0.023 g ($1.92 \times 10^{-5}$ mol) of tetrakis(triphenylphosphine)platinum (O) were introduced into a flask and reacted with stirring by heating in an oil bath at 60° C. for 8 hours and then subjected to distillation under a reduced pressure to produce 5.6 g (17.5 millimol) of n-hexylphenethyldichlorosilane.

Resultant n-hexylphenethyldichlorosilane had a boiling point of 120°~123° C./1 mmHg and $n_D^{20}$ of 1.5009. The result of elemental analysis was as follows:

measured value: C: 57.87%, H: 7.57%, Cl: 23.5%

(theoretical value: C: 58.12%, H: 7.66%, Cl: 24.51%).

Figure 1:
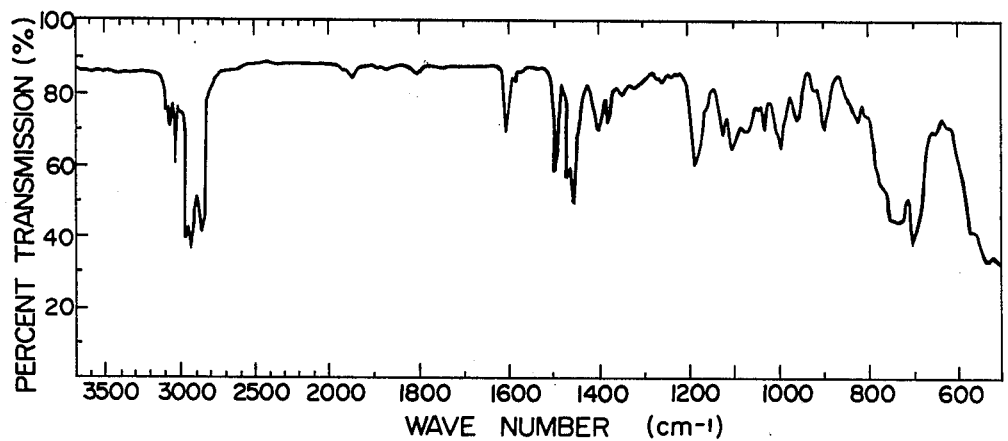
FIG. 1 is the infrared spectra of n-hexylphenethyldichlorosilane.
Figure 2:
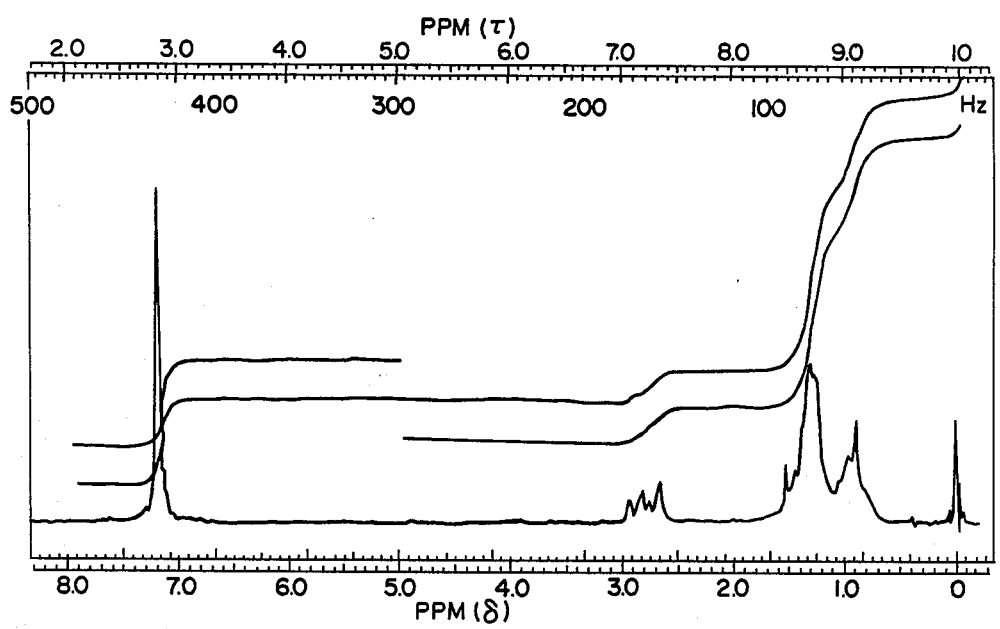
FIG. 2 is the NMR spectra of the same.

The infrared spectra of this product are shown in FIG. 1 and the neuclear magnetic resonance (NMR) spectra thereof are shown in FIG. 2. From the above-mentioned result, a formula of (n-C$_6$H$_{13}$)(C$_6$H$_5$CH$_2$CH$_2$)SiCl$_2$ was confirmed for this product.

COMPARATIVE EXAMPLE 1

Reaction was carried out as in example 1 except that a H$_2$PtCl$_6$.6H$_2$O isopropanol solution was substituted for tetrakis(triphenylphosphine)platinum (O) whereby resinous product was formed and no n-hexylphenethyldichlorosilane was obtained.

EXAMPLE 2

A procedure was carried out as in example 1 but n-dodecyldichlorosilane was substituted for n-hexyldichlorosilane whereby n-dodecylphenethyldichlorosilane was obtained.

Figure 3:
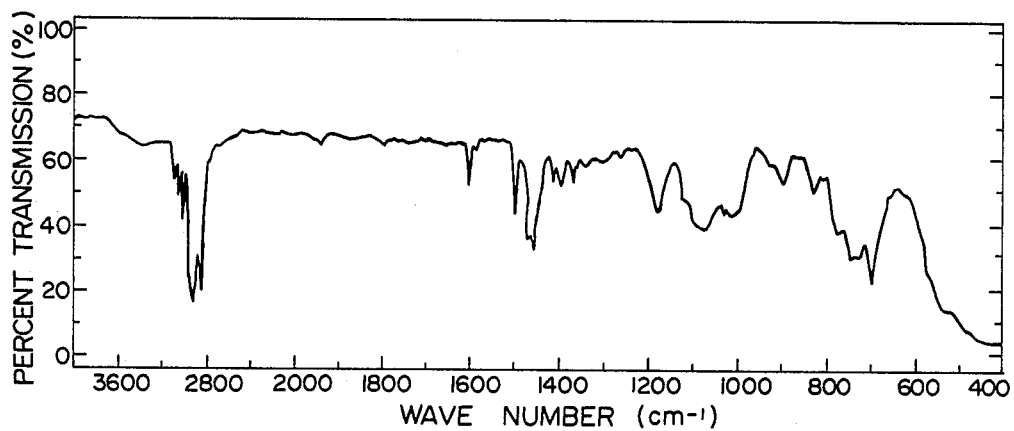
FIG. 3 is the infrared spectra of n-dodecylphenethyldichlorosilane.
Figure 4:
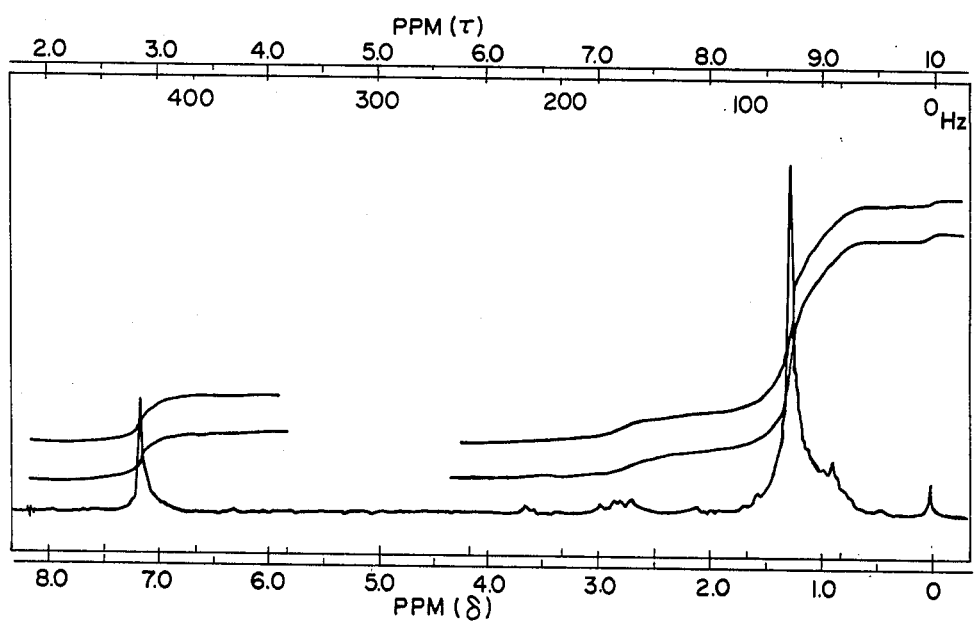
FIG. 4 is the NMR spectra of the same.

The boiling point of product was 165.2~168.0/2 mmHg. The infrared spectra of this product are shown in FIG. 3 and the NMR spectra are shown in FIG. 4.

From the above-mentioned result, a formula of (n-C$_{12}$H$_{25}$)(C$_6$H$_5$CH$_2$CH$_2$)SiCl$_2$ was confirmed for the product.

EXAMPLE 3

0.89 mol of 1-hexene, 0.08 mol % of a catalyst of tetrakis(triphenylphosphine)platinum (O) (relative to dichlorosilane) were introduced into a 500 ml pressure-proof stainless steel reactor which was then closed and cooled with a dry-ice-methanol bath. After introducing 0.64 mol of dichlorosilane through a leading pipe, the reactor was sealed and reaction was carried out by heating in an oil bath at 100° C. for 2 hours with stirring. Then this reacted liquid was transferred to a flask. 0.64 mol of styrene was added and reaction was carried out with stirring at 80° C. for 4 hours. After the reaction, distillation was carried out under a reduced pressure to obtain 0.58 mol of n-hexylphenethyldichlorosilane having a boiling point of 120°~123° C./1 mmHg.

EXAMPLE 4

25.6 g (254 millimol) of dichlorosilane, 52.3 g (502 millimol) of styrene and 0.295 g (0.237 millimol) of tetrakis(triphenylphosphine)platinum (O) were charged into a 200 ml pressure-proof stainless steel reaction tube as in Example 3, then heated in an oil bath at 150° C. for 16 hours with stirring. By the distillation of the reacted liquid carried out under a reduced pressure after the reaction, there was obtained 36.0 g of product having a boiling point of 140°~151° C./1.0 mmHg.

Figure 5:
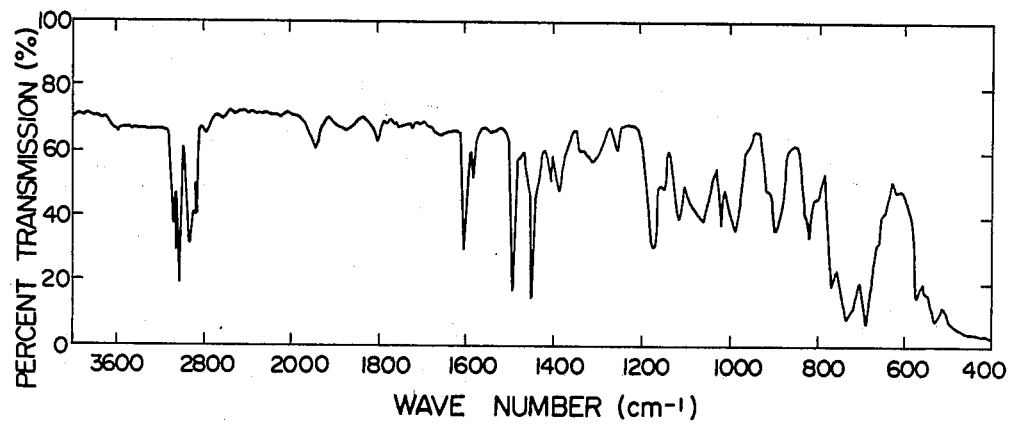
FIG. 5 is the infrared spectra of diphenethyldichlorosilane.
Figure 6:
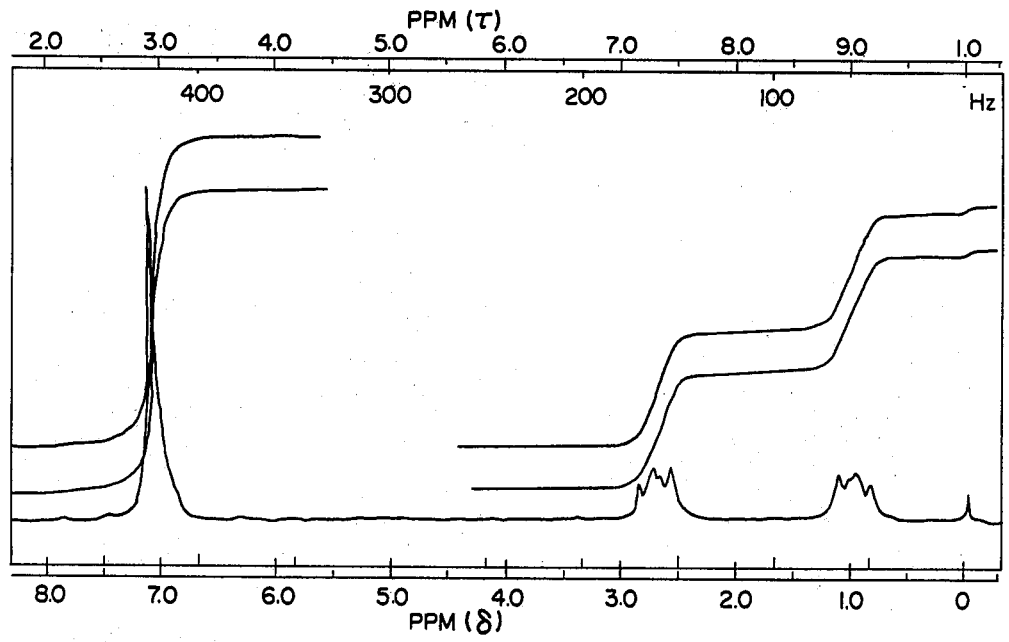
FIG. 6 is the NMR spectra of the same.

The infrared spectra of the product are shown in FIG. 5. There are observed absorptions of stretching vibration of aromatic C—H at 3000~3100 cm$^{-1}$ and deformation vibration of C—H directly connected with Si at 1260 cm$^{-1}$ but no characteristic absorption for Si—H in the neighbourhood of 2100 cm$^{-1}$. The neuclear magnetic resonance (NMR) spectra are shown in FIG. 6. Its δ value (ppm) has no signal corresponding to Si—$\underline{H}$ at 3.0~5.0, but shows signals at 0.99 corresponding to Si—C$\underline{H_2}$—, at 2.72, to —C$\underline{H_2}$—CH$_2$—C$_6$H$_5$ and at 7.12 to C$_6$$\underline{H_5}$—. Its integral value was 4:4:10.

In the mass spectra, parent ion M+ 308 appeared. From the foregoing result, the product was confirmed to be diphenethyldichlorosilane.

COMPARATIVE EXAMPLE 2

30.0 g (300 millimol) of dichlorosilane, 56.5 g (543 millimol) of styrene and 50 ml of an isopropanol solution of chloroplatinic acid [H$_2$PtCl$_6$.6H$_2$O (4.83×10$^{-6}$ mol)] were charged in a 200 ml pressure-proof stainless steel reaction tube and reaction was carried out as in example 3 by heating in an oil bath at 50° C. for 15 hours with stirring. After reaction, the reacted liquid resinified and no diphenethyldichlorosilane was obtained.

COMPARATIVE EXAMPLE 3

31.7 g (314 millimol) of dichlorosilane, 56.3 g (541 millimol) of styrene and 0.2182 g (2.36×10$^{-4}$ mol) of chlorotris(triphenylphosphine)rhodium (I) were charged into a 200 ml pressure-proof stainless steel reaction tube as in example 3 and reaction was carried out by heating in an oil bath at 150° C. for 20 hours with stirring.

After reaction, the reacted liquid was distilled under a reduced pressure, whereby 45.7 g (223 millimol) of product of monophenethyldichlorosilane was obtained but no diphenethyldichlorosilane was obtained.

EXAMPLE 5

73.2 g (725 millimol) of dichlorosilane, and 92.7 g (890 millimol) of styrene were reacted in the presence of 0.1164 g (1.68×10$^{-4}$ mol) of chlorotris(triphenylphosphine)rhodium (I) as in example 3 at 100° C. for 16 hours and then the reacted liquid was distilled to obtain 147.6 g of monophenethyldichlorosilane (b.p. 95° C./7 mmHg).

10.3 g (50 millimol) of said monophenethyldichlorosilane, 22.7 g (218 millimol) of styrene and 0.08 g (6.42×10$^{-5}$ mol) of tetrakis(triphenylphosphine)platinum (O) were charged into a 100 ml, stainless steel reaction tube and reacted by heating in an oil bath at 100° C. for 15 hours with stirring. After the reaction, the reacted liquid was distilled under a reduced pressure to obtain 13.6 g of the product having a boiling point of 141° C./1.5 mmHg.

The infrared spectra, the NMR spectra and the mass spectra of the product were the same with those of the product of example 4 and thus it was confirmed that the product was diphenethyldichlorosilane.

What is claimed is:

1. A substituted phenethyldichlorosilane having the general formula

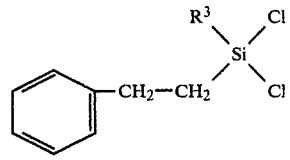

wherein R$^3$ is an alkyl group having 3-20 carbon atoms or phenethyl group.

2. A substituted phenethyldichlorosilane according to claim 1 wherein R$^3$ is an alkyl group having 3-20 carbon atoms.

3. A substituted phenethyldichlorosilane according to claim 1 wherein R$^3$ is phenethyl group of

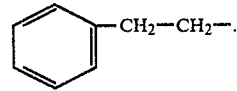

* * * * *